US00PP20732P2

(12) United States Plant Patent
Kordes

(10) Patent No.: US PP20,732 P2
(45) Date of Patent: Feb. 9, 2010

(54) SHRUB ROSE PLANT NAMED 'KORCASIMA'

(50) Latin Name: *Rosa hybrida*
Varietal Denomination: KORcasima

(75) Inventor: Wilhelm Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/228,864

(22) Filed: Aug. 15, 2008

(51) Int. Cl.
*A01H 5/00* (2006.01)

(52) U.S. Cl. ..... Plt./108

(58) Field of Classification Search ..... Plt./108
See application file for complete search history.

(56) References Cited

FOREIGN PATENT DOCUMENTS

EM 2007/1336 6/2007

*Primary Examiner*—Annette H Para

(57) ABSTRACT

A new and distinct variety of rose with long lasting, novel red flowers, and attractive foliage with good disease resistance. It exhibits bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORcasima'.

BACKGROUND OF THE INVENTION

The new variety of rose plant of the present invention originated from a controlled crossing in a breeding program of two distinct parents during the summer of 2002. The crossing was between an 'un-named seedling' and 'Insel Mainau'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORcasima'.

SUMMARY OF THE INVENTION

The new rose plant may be distinguished from its seed parent, an 'un-named seedling', by the following combination of characteristics:

1. The flower size of the 'un-named seedling' is small, while the flower size of 'KORcasima' is medium to large.
2. The petal count of the 'un-named seedling' is semi-double, while the petal count of 'KORcasima' is very double.

The new rose plant may be distinguished from its pollen parent, an 'Insel Mainau' by the following combination of characteristics:

1. The disease resistance of 'Insel Mainau' is poor, while the disease resistance of 'KORcasima' is good.
2. The height of 'Insel Mainau' is 40–50 cm, while the height of 'KORcasima' is 70–80 cm.

The objective of the hybridization was to create a new and distinct rose plant with unique qualities, such as:

1. Compact and uniform growth and flowering; when grown as a plant from cuttings;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORcasima' from all other varieties of which we are aware.

As part of a rose development program, Wilhelm Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORcasima' was selected in May, 2003 from the seedling beds to be asexually propagated for further evaluation. The first asexual propagation of 'KORcasima' was done by budding to seedling understocks in July, 2003 at the inventor's nursery in Offenseth-Sparrieshoop, Germany.

This initial and other subsequent propagations conducted in controlled environments demonstrate that 'KORcasima' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORcasima'.

Specifically illustrated in SHEET ONE is a stem exhibiting thorns; tight bud and open flower bloom; juvenile foliage and tip of stem; dissected receptacle and detached sepal; and leaves.

DETAILED BOTANICAL DESCRIPTION

The following is a description of 'KORcasima', as observed in its growth in August, 2008 in a nursery in Jackson County, Oreg. on plants of three years of age. Color references are made using The Royal Horticultural Society (London, England) Colour Chart, 2001 except where common terms of color are used.

For a comparison, several physical characteristics of the rose variety 'KORpriggos', a rose variety from the same inventor described and illustrated in U.S. Plant patent application No. 11/893,516 and filed on Aug. 15, 2007 are compared to 'KORcasima' in Chart 1.

CHART 1

| Characteristic | 'KORcasima' | 'KORpriggos' |
|---|---|---|
| Flower color, ¼ open | Upper surface: Red Group 53A. Lower surface: Red Group 53A. | Upper surface: Orange-White Group 159D. Lower surface, marginal zone: White Group 155D. Transitions to a large marginal zone of Yellow Group 2D. |
| Petal count | Very double, with 70-80 petals on average. | Double to very double, with 45-50 petals on average. |

Parents:

*Seed parent.*—An 'un-named seedling'.

*Pollen parent.*—'Insel Mainau'.

Classification:

*Botanical classification.*—*Rosa hybrida,* 'KORcasima'.

*Commercial classification.*—Shrub rose.

FLOWER AND FLOWER BUD

Blooming habit: Recurrent.

*Flower bud.*—Size: Upon opening, 20 mm in length from base of receptacle to end of bud and 18 mm in diameter at its widest point. Bud form: Short and globular. Bud color: As sepals first unfold, bud color is Red Group 53A. When ¼ open, the upper surface of petals is Red Group 53A, and the lower surface of petals is Red Group 53A. Sepals: Size: Average 18 mm long×7 mm wide. Shape: Sepals generally subulate. Sepal apex is generally cirrose. Weak foliaceous appendages on three of the five sepals. Base is flat at union with receptacle. Quantity: Five. Margins: With few stipitate glands on outer surface. Surface texture: Inner side: Covered in fine white hairs. Outer surface: Smooth. Color: Upper surface Yellow-Green Group 144A and Yellow-Green Group 144B. Lower surface Yellow-Green Group 144A.

*Receptacle.*—Surface: Smooth. Color: Yellow-Green Group 145A. Shape: Pear-shaped. Size: 6 mm (h)×6 mm (w).

*Peduncle.*—Surface: With stipitate glands. Length: 25–28 mm average length. Diameter: 1.0–1.5 mm average diameter. Color: Yellow-Green Group 145A. Strength: Strong. Borne: Multiple buds per stem. 3–9 buds per flowering stem Anthocyanin: Greyed-Red Group 178A.

Flower bloom:

*Fragrance.*—Light.

*Duration.*—Long lasting. The blooms have a duration on the plant of approximately 6 to 7 days. Senesced petals drop away cleanly.

*Size.*—Medium to large flowered garden rose. When open, the average flower diameter is 65–75 mm and the average flower height is 35 mm.

*Form.*—Open flowers express quartered rosette shape. Shape of flower when viewed from the side: Upon opening, upper part: Flattened convex. Upon opening, lower part: Concave. Open flower, upper part: Flattened convex — convex. Open flower, lower part: Concave.

Color:

*Upon opening, petals.*—Outermost petals: Outer Side: Red Group 53B. Inner Side: Red Group 53A. Innermost petals: Outer Side: Red Group 53B. Inner Side: Red Group 53A.

*Upon opening, basal petal spots.*—Basal petal spot, outermost petals: Outer Side: Green-Yellow Group 1C. Inner Side: Green-Yellow Group 1C. Basal petal spot, innermost petals: Outer Side: Green-Yellow Group 1D. Inner Side: Green-Yellow Group 1D.

*After opening petals.*—Outermost petals: Outer Side: Red Group 53B. Inner Side: Red Group 46A. Innermost petals: Outer Side: Red Group 53B. Inner Side: Red Group 53A.

*After opening, basal petal spots.*—Basal petal spot, outermost petals: Outer Side: Green-Yellow Group 1C. Inner Side: Green-Yellow Group 1C. Basal petal spot, innermost petals: Outer Side: Green-Yellow Group 1D. Inner Side: Green-Yellow Group 1D. Variegations: None.

General tonality: On open flower Red Group 53A. No change in the general tonality at the end of the 6th day. Afterwards, general tonality is Red-Purple Group 60A.

Petals:

*Petal count.*—Approximately 70–80 petals under normal conditions.

*Petal reflex.*—Petals reflex slightly.

*Petal edge.*—Entire and smooth.

*Petal shape.*—Obovate. Apex shape is round. Shape of base is acute.

*Petal size.*—25 mm long; 20 mm wide.

*Thickness.*—Thin.

*Petal arrangement.*—Generally in a regular pattern with overlapping edges.

Petaloids: Present.

*Petaloid count.*—Average of 2–5 per flower.

*Petaloid edge.*—Smooth.

*Petaloid texture.*—Smooth.

*Petaloid shape.*—Elongated. Entire. Shape of apex is round, shape of base is pointed.

*Petaloid size.*—Petaloids are 4–5 mm long and 3–4 mm wide.

*Petaloid color.*—Color of inner side is Red Group 53A. Color of outer side is Red Group 53A.

Reproductive organs:

*Pistils.*—Approximately 35–40 present. Stigmas: Location: Superior in position to anthers. Color: Greyed-Yellow Group 162D. Styles: Length: 6 mm long. Color: Green-Yellow Group 1B.

*Stamens.*—Approximately 10–15 on average and regularly arranged. Anthers: Size: 2 mm long. Color: Yellow-Orange Group 16B. Pollen: Absent. Filaments: Color: Green-Yellow Group 1C. Length: 2–3 mm.

THE PLANT

*Plant growth.*—Vigorous. Bushy habit. When grown as a budded nursery plant the average plant height is 70–80 cm and the average plant width is 60–70 cm.

*Stems.*—Stem color: Young wood: Yellow-Green Group 144B. Older wood: Yellow-Green Group 144B. Stem surface: Young wood: Smooth. Older wood: Smooth.

*Prickles.*—Present. Incidence: 15–20 per 10 cm of stem. Size: Average length: 8 mm. Color: Immature prickles: Yellow-Green Group 146D. Mature prickles: Yellow-Green Group 146D. Senescing to Greyed-Yellow Group 160B. Shape: Concave. Anthocyanin: Greyed-Red Group 178A.

*Leaves and leaflets.*—Normally 5–7 leaflets on normal leaves in middle of the stem. Venation pattern: Pyramidal net pattern. Leaf size: 125 mm (l)×75 mm (w). Quantity: Average. Texture: Upper side of leaflet: Glossy and smooth. Under side of leaflet: Glossy and smooth. Color, mature foliage: Upper Leaf Surface: Green Group 137A. Lower Leaf Surface: Yellow-Green Group 148B. Color, juvenile foliage: Upper Leaf Surface: Green Group 138A. Lower Leaf Surface: Yellow-Green Group 148B. Anthocyanin intonation: Greyed-Purple Group 187A.

*Stipules.*—Size: 16 mm long. 7 mm between the tips of the stipule. Main body of stipule 8 mm in width. Shape: Longitudinally flanged or winged along middle. Stipule color: Green Group 138A and Yellow-Green Group 145A. Presence of stipitate glands: Present on margins. Margins: Serrated. With stipitate glands and fine, white hairs. Anthocyanin intonation: Greyed-Purple Group 183B.

*Petiole.*—Length: 11 mm. Diameter: 1.0 mm. Petiole color: Green Group 138A. Underneath: An occasional prickle. Stipitate glands: Present on margins. Petiole Rachis: Length: 12–16 mm. Diameter: 1.0 mm. Color: Green Group 138A. Margins: With stipitate glands. Prickles: An occasional prickle underneath.

*Leaflets.*—Size: Average size of the terminal leaflet is 45 mm (l)×30 mm (w). Shape: Ovate. Base: Ovate. Apex: Acute Margins: Serrated. Texture: Thick and leathery.

Hips / seed formation: None observed.

Winter hardiness: To date, the variety has been grown successfully in Zone 5.

Disease resistance: Above average resistance to powdery mildew and Black spot disease under normal growing conditions.

I claim:

1. A new and distinct variety of rose plant characterized by the following combination of characteristics:

(a) Forms attractive, long lasting red flowers;

(b) Exhibits bushy growth habit;

(c) Propagates well using traditional methods, and;

(d) Exhibits very good resistance to disease under normal growing conditions, substantially as herein illustrated and described.

* * * * *

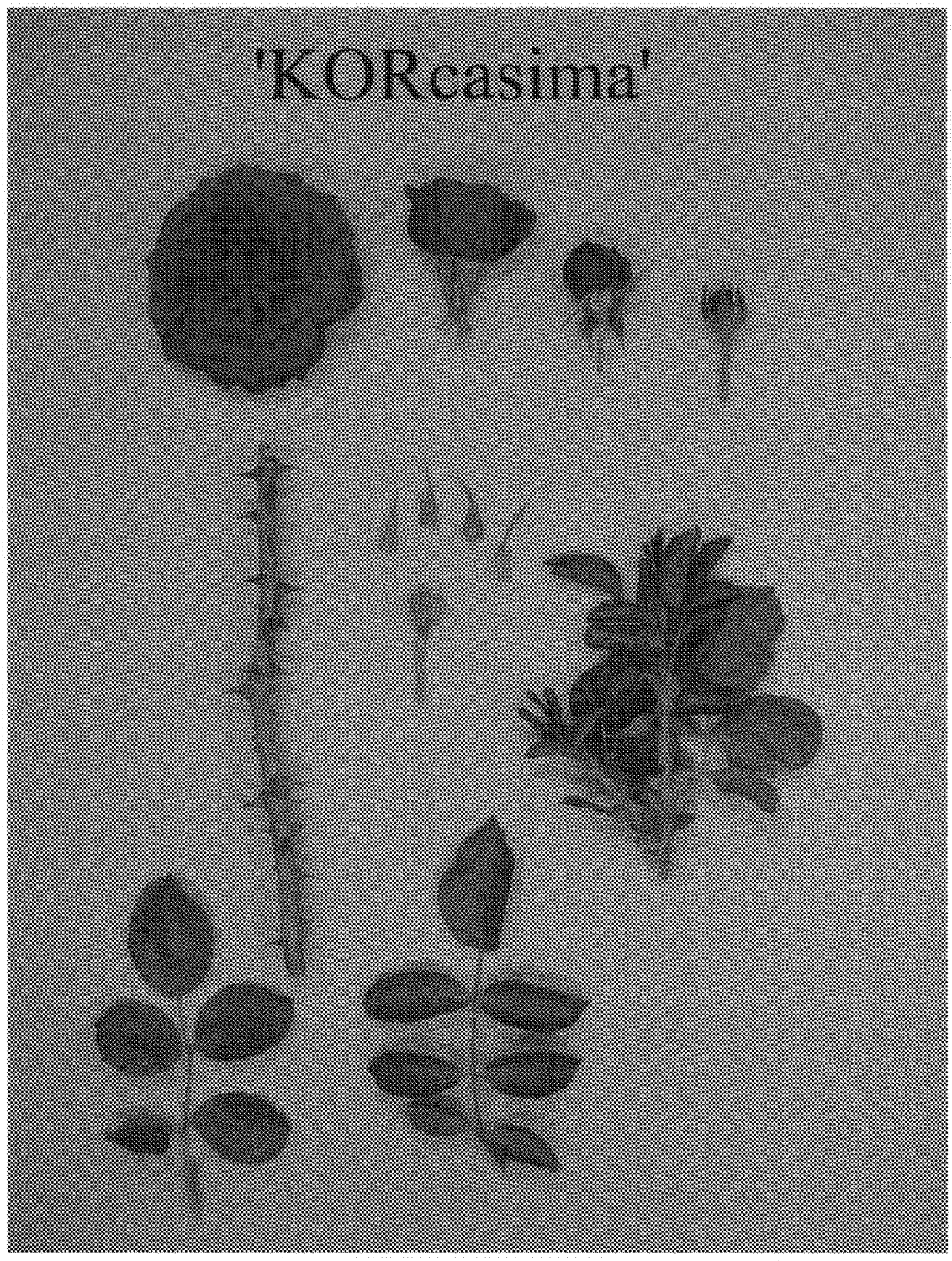
'KORcasima'